(12) United States Patent
Klinder (10) Patent No.: US 10,113,904 B2
(45) Date of Patent: Oct. 30, 2018

(54) OPTICAL SENSOR

(71) Applicant: SICK ENGINEERING GMBH, Ottendorf-Okrilla (DE)

(72) Inventor: Kai Klinder, Ottendorf-Okrilla (DE)

(73) Assignee: SICK ENGINEERING GMBH, Ottendorf-Okrilla (DE)

( * ) Notice: Subject to any disclaimer, the term of this patent is extended or adjusted under 35 U.S.C. 154(b) by 118 days.

(21) Appl. No.: 15/407,431

(22) Filed: Jan. 17, 2017

(65) Prior Publication Data

US 2017/0205279 A1 Jul. 20, 2017

(30) Foreign Application Priority Data

Jan. 18, 2016 (EP) .................................... 16151704

(51) Int. Cl.
*H01J 40/14* (2006.01)
*G01J 1/04* (2006.01)
(Continued)

(52) U.S. Cl.
CPC ........... *G01J 1/0414* (2013.01); *G01J 1/0228* (2013.01); *G01J 1/0295* (2013.01); *G02B 26/0833* (2013.01)

(58) Field of Classification Search
CPC ...... G01J 1/0403; G01J 1/0407; G01J 1/0411; G01J 1/0414; G02B 26/0816;
(Continued)

(56) References Cited

U.S. PATENT DOCUMENTS 4,578,762 A 3/1986 Wong
8,325,409 B2 12/2012 Sethuraman et al.
(Continued)

FOREIGN PATENT DOCUMENTS

EP 2787332 A1 10/2014
JP H03215718 A 9/1991
(Continued)

OTHER PUBLICATIONS

Japanese notice of allowance dated Feb. 20, 2018 for corresponding patent application No. 2017-003862 with English translation attached.

*Primary Examiner* — Kevin Pyo
(74) *Attorney, Agent, or Firm* — Nath, Goldberg & Meyer; Jerald L. Meyer (57) ABSTRACT

An optical sensor comprises a light transmitter; a light receiver; an evaluation unit; at least one mirror unit that comprises a plurality of micromirror elements having an at least regionally reflective surface and comprising an electrode arrangement connected to the micromirror elements; and a control device that is configured to adjust the mirror unit between at least two different functional states by controlling the electrode arrangement. The mirror unit comprises an at least substantially transparent substrate at which the micromirror elements are arranged. The control device is configured to temporarily set the mirror unit into a transmission state in which the micromirror elements are in an open position and light radiation incident onto the mirror unit moves past the micromirror elements through the transparent substrate.

20 Claims, 7 Drawing Sheets

(51) Int. Cl.
*G01J 1/02* (2006.01)
*G02B 26/08* (2006.01)

(58) Field of Classification Search
CPC ............ G02B 26/0833; G02B 26/0841; G02B 26/0858; G02B 26/10
USPC .......................... 250/234; 359/298, 316, 318
See application file for complete search history.

(56) References Cited

U.S. PATENT DOCUMENTS

| | | |
|---|---|---|
| 2004/0125361 A1* | 7/2004 | Riza ..................... G01J 1/4257 356/121 |
| 2006/0187528 A1 | 8/2006 | Hagood et al. |
| 2006/0268268 A1 | 11/2006 | Yokota |
| 2014/0299774 A1 | 10/2014 | Kaufmann et al. |
| 2017/0219706 A1* | 8/2017 | Baldischweiler ..... G01S 7/4817 |

FOREIGN PATENT DOCUMENTS

| | | |
|---|---|---|
| JP | H08149355 A | 6/1996 |
| JP | 2003014629 A | 1/2003 |
| JP | 2008510986 A | 4/2008 |
| WO | 2006087219 A1 | 8/2006 |
| WO | 2014162537 A1 | 10/2014 |

\* cited by examiner

OPTICAL SENSOR

The present invention relates to an optical sensor comprising a light transmitter for transmitting transmitted light beams into a measured zone; a light receiver for receiving received light beams from the measured zone; an evaluation unit for determining a property of the measured zone using the received light beams received by the light receiver; at least one mirror unit for controlling the transmitted light beams and/or the received light beams, with the mirror unit comprising a plurality of micromirror elements having at least regionally reflective surface and comprising an electrode arrangement electrically connected to the micromirror elements; and a control device that is configured to adjust the at least one mirror unit between at least two different functional states by controlling the electrode arrangement.

Such sensors are used in a variety of ways for monitoring work and measurement work, for example in the form of dust measuring units, fog measuring units, gas concentration measuring units, spectrometers and the like. Depending on the application, the light transmitted through the measured zone, the light reflected from the measured hone or the light scattered out of the measured zone into a specific spatial angular region is detected by the light receiver in this process. A further area of use of optical sensors is the recognition of objects or the determination of specific properties of objects that are located in the measured zone. Light sensors, light barriers, light grids, color sensors or scanners are e.g. used for work of this kind.

Mirror units that are based on an arrangement of movable and electrically contacted micromirror elements are also called micromirror arrays or MEMS mirror arrays (MEMS=microelectromechanical systems) in the technical field. In comparison with bean shaping optics having movable macroscopic mirrors or beam splitters, micromirror arrays have the advantage that the functional state of the sensor can be adjusted purely electrically and with a short switching time. In addition, the space requirement of micromirror arrays is small.

The micromirror elements can be designed as flat, planar or curved blades that are pivotably supported at a carrier component. Such micromirror elements are also called "vanes" and are disclosed, for example, in U.S. Pat. No. 8,325,409 B2.

Micromirror arrays are typically operated exclusively in reflection in optical sensors. The two functional states of the mirror unit in this respect correspond to different angles of reflection, that is the incident light is deflected to a different extent depending on the functional state. The design possibilities for the optical paths of the sensor associated with the functional states are not restricted in this respect.

It is an object of the invention to provide an optical sensor of the initially named kind that has extended design possibilities.

The object is satisfied by an optical sensor having the features of claim 1.

Provision is made in accordance with the invention that the mirror unit comprises an at least substantially transparent substrate at which the micromirror elements are arranged and that the control device is configured to temporarily set the mirror unit into a transmission state in which the micromirror elements are in an open position and light radiation incident onto the mirror unit moves past the micromirror elements through the transparent substrate.

It has been recognized in accordance with the invention that optical paths are defined in sensors by the temporary operation of a micromirror array in transmission that were previously only possible while accepting considerable disadvantages. For example, a beam guidance free of deflection can be effected without the use of movable macroscopic mirrors or beam splitters. A sensor in accordance with the invention is thus particularly compact, inexpensive and maintenance-friendly. The dispensing with of moved macroscopic parts additionally allows a power-saving operation.

The micromirror elements can each be pivotable between the open position and a closed position. The micromirror elements preferably each comprise a silicon oxynitride substrate having a reflective aluminum coating. The size of the micromirror elements preferably amounts to at most 1 $mm^2$ and particularly preferably at most 0.5 $mm^2$. To ensure an interference-free irradiation of the mirror unit in the transmission state, the electrode arrangement can comprise a transparent layer that is applied to the substrate and that is in electrical contact with the micromirror elements.

Provision can be made that the transmitted light beams move through the substrate of the mirror unit without passing through the measured zone to the light receiver when the mirror unit is set into the transmission state. This allows the detection in a simple manner of the intensity of the unattenuated light, for example for reference or regulation purposes.

The control device can in particular be configured to set the mirror unit into the transmission state on the presence of a control criterion, a comparison criterion or a correction criterion. It is frequently important for the reliability of the measurement to temporarily provide for the reception of a reference signal that is not influenced by the measured zone during the sensor operation. The reception of an unattenuated reference signal is in particular significant for a power regulation of the light transmitter, for a correction of the zero point drift and for a contamination inspection.

The micromirror elements can each be tilted by a tilt angle with respect to a light incidence surface of the substrate when the mirror unit is set into the transmission state. The tilt angle preferably amounts to between 40° and 50°. The tilt angle can amount to approximately 45°, for example.

In accordance with a preferred embodiment of the invention, the mirror unit is arranged such that the micromirror elements are aligned at least substantially in parallel with a main direction of incidence of the transmitted light beams or of the received light beams when the mirror unit is set into the transmission state. In this embodiment, the flat sides of the micromirror elements therefore extend in parallel with the incident light when the mirror unit is set into the transmission state. The light incident onto the mirror unit is thereby practically not blocked by the open micromirror elements so that the transmission losses are small.

The control device is preferably configured to temporarily set the at least one mirror unit into reflection state in which the micromirror elements at least partly cover a light incidence surface or a light exit surface of the mirror unit, preferably at least 75% thereof, and particularly preferably at least 90% thereof. A high degree of coverage allows a particularly low-loss beam deflection.

The control device can be configured to adjust the mirror unit cyclically between the reflection state and the transmission state during sensor operation. It is thereby possible to carry out the above-mentioned control measures, comparison measures or correction measures so-to-say constantly during the sensor operation, whereby a particularly exact and reliable operation results and unwanted data gaps are avoided. On use of a movable macroscopic mirror, a cyclic carrying out of control measures, compensation measures or correction measures is generally impractical due to the relatively long switching time.

A specific embodiment of the invention provides that the light transmitter and the light receiver are arranged on a straight-line optical path and the measured zone is spaced apart from the straight-line optical path, with the mirror unit decoupling the transmitted light beams from the straight-line optical path and deflecting them into the measured zone when said mirror unit is set into the reflection state. The transmitted light beams in this embodiment move directly to the light receiver without passing through the measured zone when the mirror unit is set into the transmission state. A particularly reliable and non-falsified detection of the output intensity of the light transmitter is thereby possible. A calibration element such as a turbidity filter can be arranged in the straight-line optical path. This e.g. allows a coordination of the output power of the light transmitter with the sensitivity of the light receiver.

The sensor can comprise a further mirror unit that comprises an at least substantially transparent substrate having micromirror elements arranged thereat and that can be adjusted between a transmission state and a reflection state, with the further mirror unit coupling the received light beams exiting the measured zone into the straight-line optical path when it is set into the reflection state. Since both mirror units can adopt a transmission state, a direct and straight-line beam guidance from the light transmitter up to the light receiver can also be provided in this embodiment.

In accordance with a further embodiment of the invention, the micromirror elements can be individually controlled by respective individual electrodes of the electrode arrangement. This expands the possibilities for use of the mirror unit since the micromirror elements can, for example, only be opened regionally. On an individual controllability of the micromirror elements, the mirror unit can adopt a lot more than two different functional states.

The control device can in particular be configured to temporarily set the mirror unit into a partly transmitting state in which only some of the micromirror elements are in an open position by controlling the individual electrodes. In the partly transmitting state, some of the light incident onto the mirror unit moves through the transparent substrate and some is reflected. The degree of transmission of the mirror unit can in this manner be set to a desired value via the control device. The control device can be configured for test purposes to set a mirror unit at the receiver side into the reflection state, on the one hand, and to set a mirror unit at the transmitter side into a partly transmitting state, on the other hand. The portion of the incident light moving through the mirror unit at the transmitter side is blocked by the mirror unit at the receiver side so that the amount of light moving to the light receiver can be reduced in stages in this manner in order thus to carry out a "span test" for example.

In accordance with a further embodiment of the invention, the control device is configured to set the mirror unit at least temporarily into an imaging state by controlling the individual electrodes, in which state the micromirror elements are tilted by different tilt angles with respect to a light incidence surface or a light exit surface of the substrate such that the mirror unit overall defines a concavely or convexly arranged mirror surface. It is meant hereby that the total extent of the mirror surface approximately resulting due to the differently tilted micromirror elements and ultimately formed by consecutive planar sections maps an arched macroscopic mirror having a continuous curvature. The transmitted light beams or the received light beams can thus e.g. be focused onto a specific region by the mirror unit.

Provision can in particular be made that the light transmitter and the mirror unit are arranged in a closed housing which comprises at least one measurement window and that the mirror unit effects a focusing of the transmitted light beams on a surface of the measurement window when it is set into the imaging state. An intense illumination of the window surface is thereby possible, which can be used, for example, for a contamination inspection. A contamination sensor in the form of an additional light receiver can be arranged in the housing to detect the light reflected and/or scattered by deposits. Such a contamination sensor is preferably arranged in the direct environment of the measurement window.

The light transmitter and the light receiver can be arranged in a closed housing that comprises at least one measurement window, with the measured zone being located outside the housing and the sensor comprising a reflector that directs the light beams back into the housing after passing through the measured zone. This embodiment is in particular suitable for explosion-proof devices. The measurement window can be slightly slanted to keep the losses due to reflection low at the interfaces.

The mirror unit can be integrated into the reflector. When the mirror unit integrated into the reflector is set into the transmission state, no light is reflected back into the sensor housing so that the light receiver exclusively detects scattered light from the measured zone. This can be utilized for a direct scattered light measurement. To avoid an unwanted light emission into the environment, the reflector can comprise a light trap that is arranged behind the mirror unit, viewed from the housing. In accordance with a special embodiment, a further mirror unit that is aligned in the opposite direction and has a transparent substrate is integrated into the reflector.

The reflector can also have a plurality of mirror units such as are described above and that are arranged in the configuration of a cat's eye. A relatively large-surface reflector can in this manner be assembled from compact micromirror arrays.

A further embodiment of the invention provides that the sensor comprises at least one actuator for moving and/or rotating the mirror unit. The transmitted light beam can be exactly aligned onto the reflector by means of the actuator. The actuator is preferably configured as a piezoelectric actuator. Position sensors, for example in the form of further light receivers, can be arranged at the reflector to facilitate the alignment procedure.

The invention also relates to an optical sensor in accordance with claim 20 comprising a light transmitter for transmitting transmitted light beams into a measured zone; a light receiver for receiving received light beams from the measured zone; an evaluation unit for determining a property of the measured zone using the received light beams received by the light receiver; at least one mirror unit for controlling the transmitted light beams and/or the received light beams, with the mirror unit comprising a plurality of micromirror elements having at least regionally reflective surface and comprising an electrode arrangement electrically connected to the micromirror elements; and a control device that is configured to adjust the at least one mirror unit between at least two different functional states by controlling the electrode arrangement.

Provision is made in the embodiment of the invention in accordance with claim 20 that the electrode arrangement comprises a plurality of individual electrodes by which the micromirror elements can be individually controlled and that the control device is configured to temporarily set the mirror unit into an imaging state by controlling the individual electrodes, in which state the micromirror elements are tilted by different tilt angles with respect to a light incidence surface or to a light exit surface of the mirror unit such that the mirror unit overall defines a concavely or convexly arched mirror surface.

As explained above, an approximation of the total extent of the mirror surface to the extent of an arched macroscopic mirror having a continuous curvature is meant by this. The transmitted light beams or the received light beams can in particular be focused onto a specific region by a direct controlling of the individual electrodes, for example onto the surface of a measurement window, for example to determine the degree of contamination of the measurement window via the detection of the light reflected and/or scattered back by the window surface. On excessive contamination, the control device can provide for the output of a warning signal or maintenance signal.

The principles in accordance with the invention can generally be used in all conventional types of optical sensors such as in light sensors, light barriers, light grids, scanners and the like. The advantages of the invention, however, in particular apply with transmissiometers and scattered light measuring devices.

Further developments of the invention are also set forth in the dependent claims, in the description and in the enclosed drawing.

The invention will be explained in the following by way of example with reference to the drawing.

Figure 1:
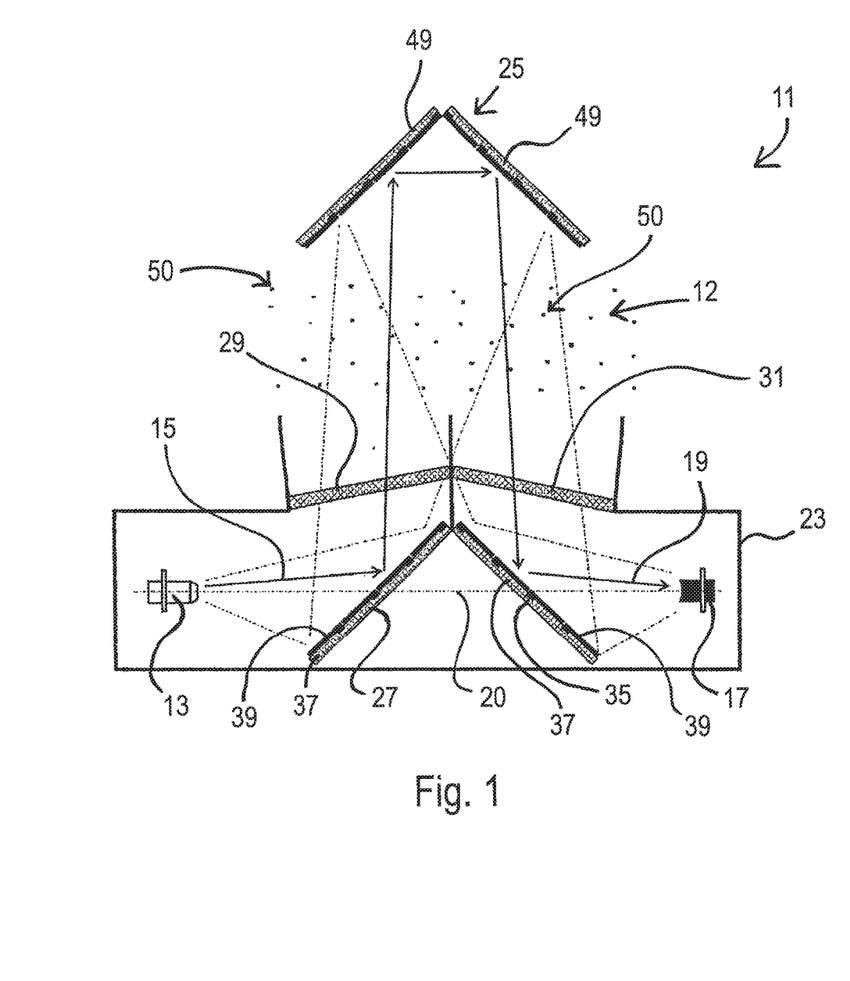
FIG. 1 is a schematic diagram of an embodiment of an optical sensor in accordance with the invention in a normal mode.

The optical sensor 11 only shown schematically in FIG. 1, here in the embodiment of a dust measurement device for determining the concentration of dust particulates 50 present in a measured zone 12, comprises a light transmitter 13 for transmitting transmitted light beams 15 and a light receiver 17 for receiving received light beams 19. The light transmitter 13 can be configured as a light emitting diode or as a laser diode. The light receiver 17 can be a simple photodiode or a spatially resolving detector such as a diode array or a CCD array. Respective beam shaping optics can be associated with the light transmitter 13 and the light receiver 17, which is, however, not shown in FIG. 1. As shown, the light transmitter 13 and the light receiver 17 face one another and have a common optical axis 20, that is the light transmitter 13 and the light receiver 17 are arranged on a straight-line optical path.

In the embodiment shown, the optical sensor 11 is designed in two parts, with a first part being formed by a closed base housing 23 and the other part being formed by a reflector 25. The light transmitter 13 and the light receiver 17 are accommodated in the closed, preferably explosion-protected base housing 23 while the measured zone 12 is located outside the base housing 23.

To detect the dust concentration in the measured zone 12, the transmitted light beams 15 are deflected by approximately 90° by a first mirror unit 27 so that they exit the base housing 23 through a first measurement window 29, pass through the measured zone 12 and are incident onto the reflector 25. The reflector 25 effects a direct re-reflection of the incident light so that it passes through the measured zone 12 again, enters into the base housing 23 again through a second measurement window 31 as received light beams 19 and is deflected by a second mirror unit 35 in the direction of the light receiver 17.

An electronic evaluation unit, not shown, is connected to the light receiver 17 and is able to determine the dust concentration in the measured zone 12 using the received light beams 19 received from the light receiver 17 and to output a corresponding dust concentration signal.

Figure 2:
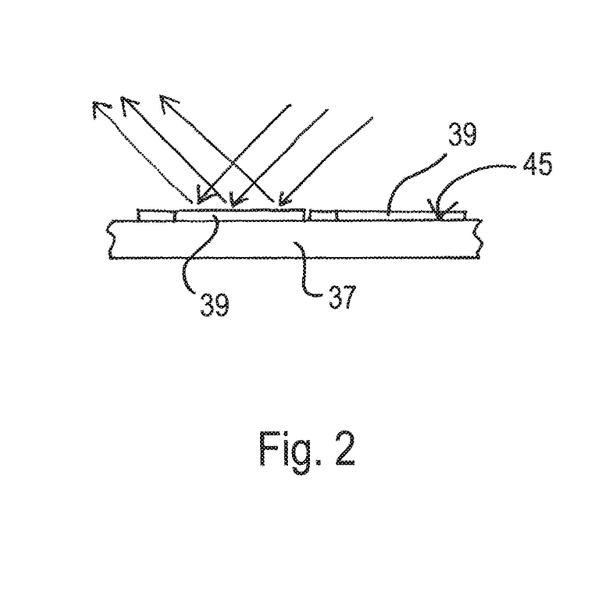
FIG. 2 is an enlarged part representation of a mirror unit to be used in an optical sensor in accordance with the invention, with micromirror elements of the mirror unit being in a closed position.
Figure 3:
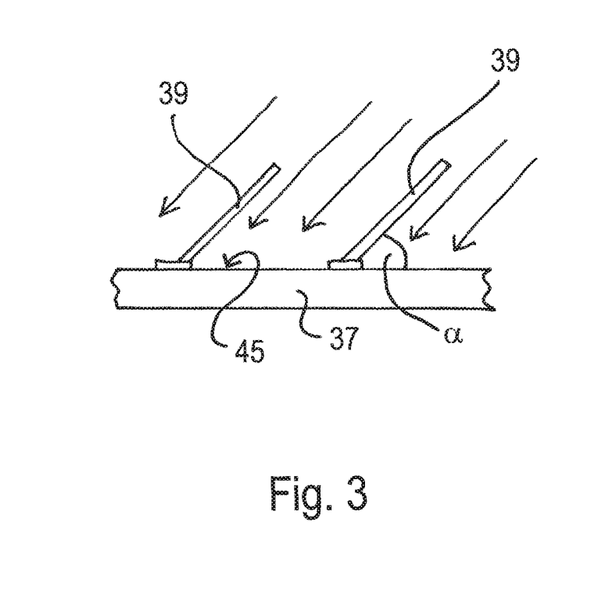
FIG. 3 shows the mirror unit shown in FIG. 2 with micromirror elements that are in an open position.

The two mirror units 27, 35 shown individually in FIGS. 2 and 3 each have a plate-like substrate 37 that is at least transparent for the wavelength range in which the light transmitter 13 irradiates light. A plurality of micromirror elements 39 in the form of flat, reflective blades are pivotably arranged at the transparent substrate 37. The micromirror elements 39 can each comprise a silicon oxynitride substrate having a reflective aluminum coating and can have a size of approximately 0.5 mm$^2$. For reasons of simplicity, only four micromirror elements 39 are shown per substrate 37 in FIG. 1. In practice, mirror units configured as micromirror arrays have substantially more micromirror elements per substrate.

Each of the micromirror elements 39 is electrically connected to associated transparent electrodes (not shown). The micromirror elements 39 can selectively be closed, as shown in FIG. 2, or open, as shown in FIG. 3, by applying suitable voltages to the electrodes.

When the micromirror elements 39 are in the closed position, as shown in FIG. 2, they are disposed transversely to the light incidence surface 45 of the substrate 37 and therefore reflect the incident light, as is shown by arrows. The respective mirror unit 27, 35 is then in a reflective state. The micromirror elements 39 preferably cover at least 90% of the light incidence surface when the mirror unit 27, 35 is in the reflective state.

When the micromirror elements 39 are in the open position, as shown in FIG. 3, they are tilted by a tilt angle $\alpha$ of approximately 45° with respect to the light incidence surface 45. Each of the mirror units 27, 35 is furthermore arranged such that their micromirror elements 39 are aligned at least substantially in parallel with a main direction of incidence of the transmitted light beams or of the received light beams when they are in the open position. The respective mirror unit 27, 35 is then in a transmission state in which light radiation incident onto the mirror unit 27, 35 moves past the micromirror elements 39 through the transparent substrate 37.

The reflector 25 comprises an arrangement of reflector mirror units 49 that are configured and arranged exactly as the first mirror unit 27 and the second mirror unit 35. Two reflector mirror units 49 are shown in FIG. 1 that are arranged next to one another and are angled with respect to one another. The reflector 25 could also comprise more than two reflector mirror units 49 that are arranged next to one another and are alternately tilted, that is that have the configuration of a cat's eye. This configuration allows the provision of a relatively large reflector surface with a simultaneously small depth of the reflector.

A control device, not shown, of the sensor 11 is configured to adjust the mirror units 27, 35 between the transmission state, the reflection state and optionally further functional states in dependence on the operating state of the sensor 11, as will be shown more precisely in the following.

If, as shown in FIG. 1, both the first mirror unit 27 and the second mirror unit 35 are set into the reflection state, the transmitted light beams 15 are decoupled from the straight-line optical path and are coupled back into the straight-line optical path as transmitted light rays 19 after passing through the measured zone 12 twice. This corresponds to a normal mode of the sensor 11.

Figure 4:
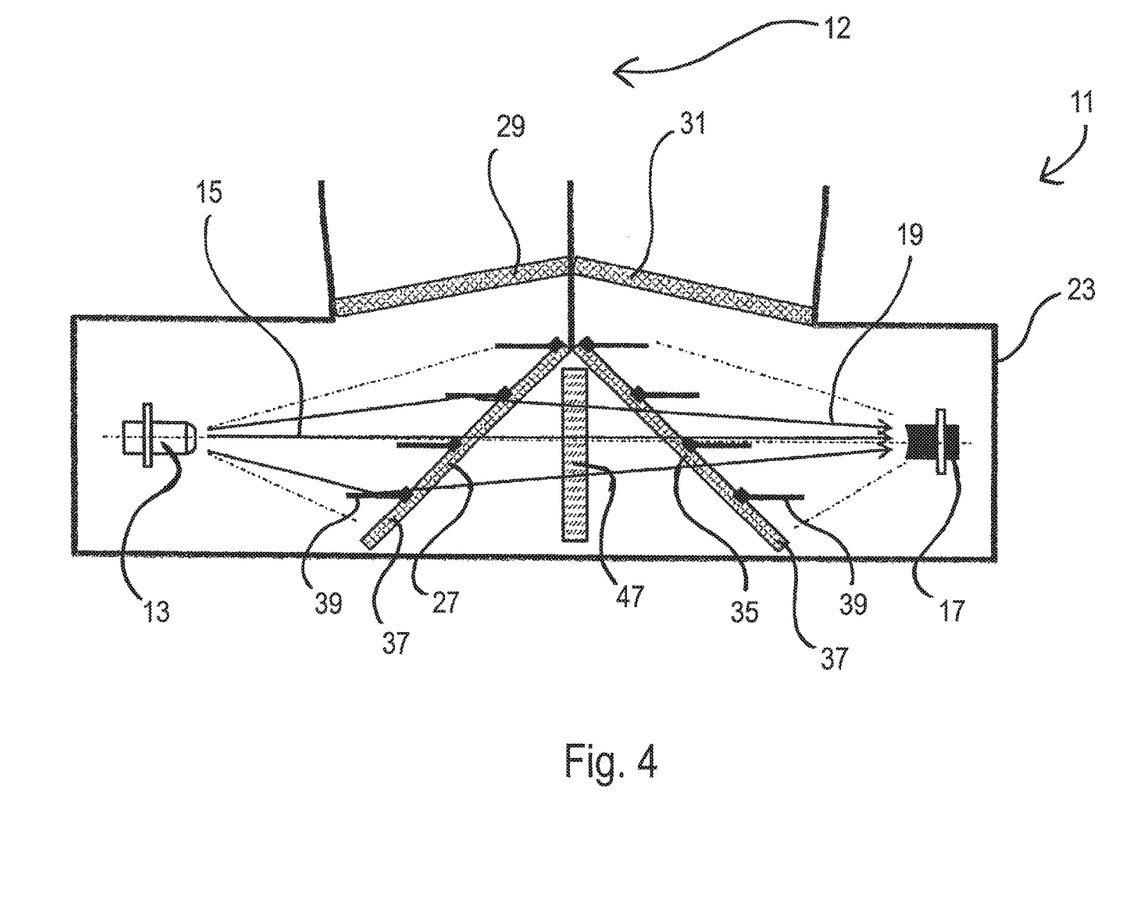
FIG. 4 shows a part of the sensor shown in FIG. 1 in a control mode.

If, in contrast, as shown in FIG. 4, both the first mirror unit 27 and the second mirror unit 35 are set into the transmission state, the transmitted light beams 15 move through the substrates 37 of the first mirror unit 27 and of the second mirror unit 35 without passing through the measured zone 12 to the light receiver 17. A calibrated turbidity filter 47 is arranged between the two mirror units 27, 35. The configuration of the sensor 11 shown in FIG. 4 corresponds to a control mode in which the output power of the light transmitter 13 is determined and/or adapted.

Figure 5:
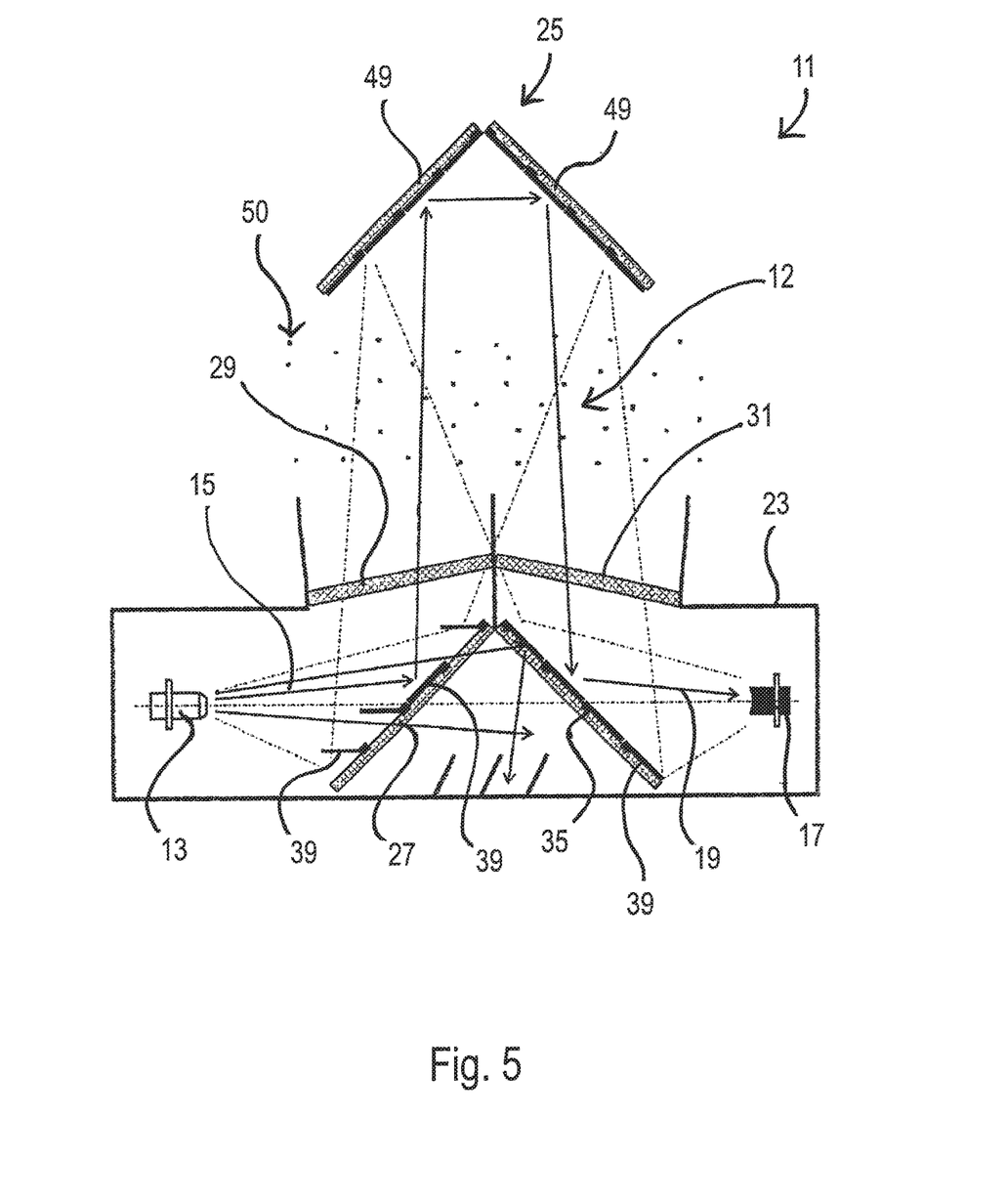
FIG. 5 shows a part of the sensor shown in FIG. 1 in a test mode.

FIG. 5 shows a further operating state of a sensor 11 in accordance with the invention in which the second mirror unit 35 is set into the reflection state, whereas the first mirror unit 27 is set into a partly transmitting state. The partly transmitting state is achieved in that some of the micromirror elements 39 are set into the open position and other ones of the micromirror elements 39 are set into the closed position. The amount of light moving back to the light receiver 17 can thereby be reduced in stages with an unchanging output power of the light transmitter 13 in order thus e.g. to carry out a "span test" in a test mode.

Figure 6:
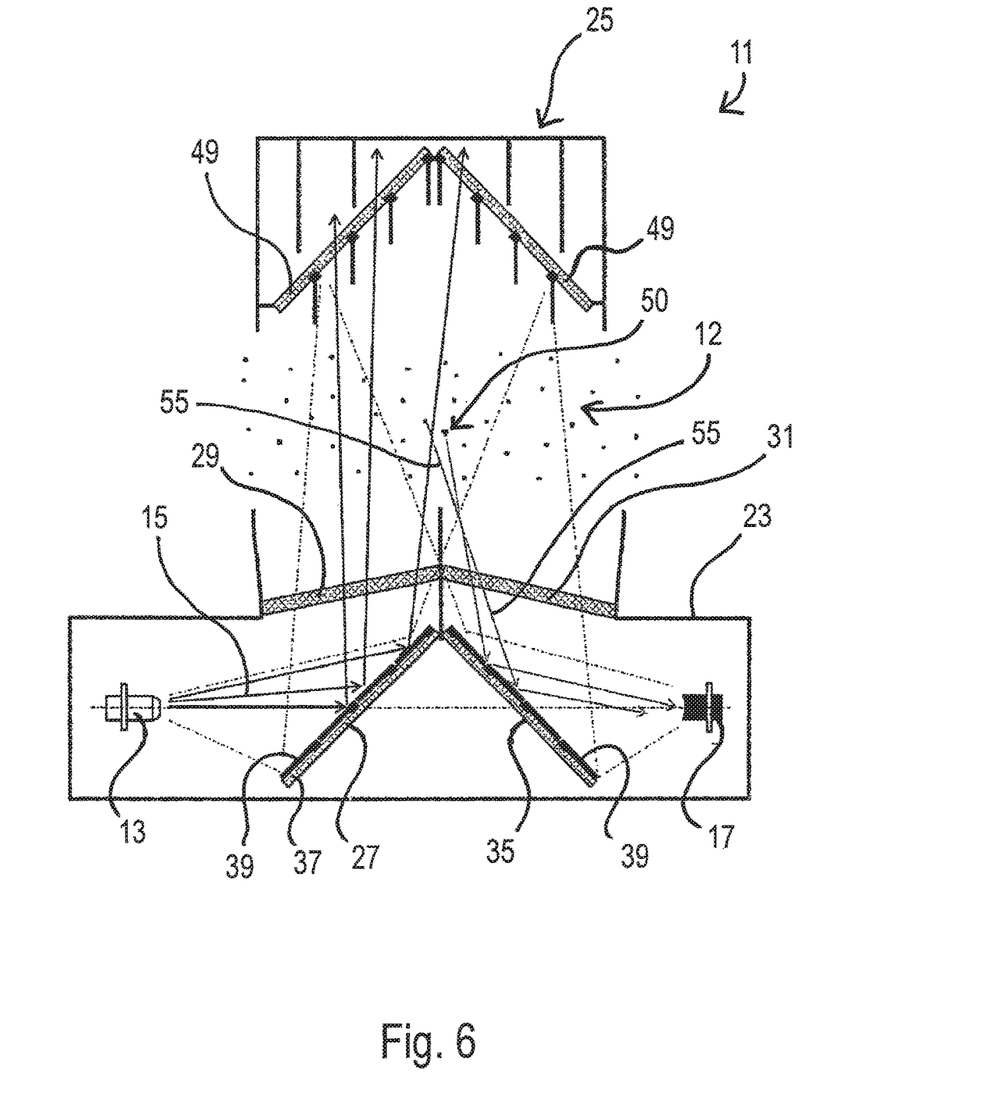
FIG. 6 shows a part of the sensor shown in FIG. 1 in a scattered light detection mode.

In the operating state shown in FIG. 6, the first mirror unit 27 and the second mirror unit 35 are set into the reflection state, whereas the reflector mirror units 49 are each set into the transmission state. The reflector 25 then acts as a light trap and does not allow any reflected light to move back to the base housing 23. Only light beams 55 scattered at dust particulates 50 arrive at the light receiver 17. A pure scattered light measurement can thus take place in this operating state. A determination of a size distribution of the dust particulates 50 is possible by combining a transmission measurement and a scattered light measurement.

Figure 7:
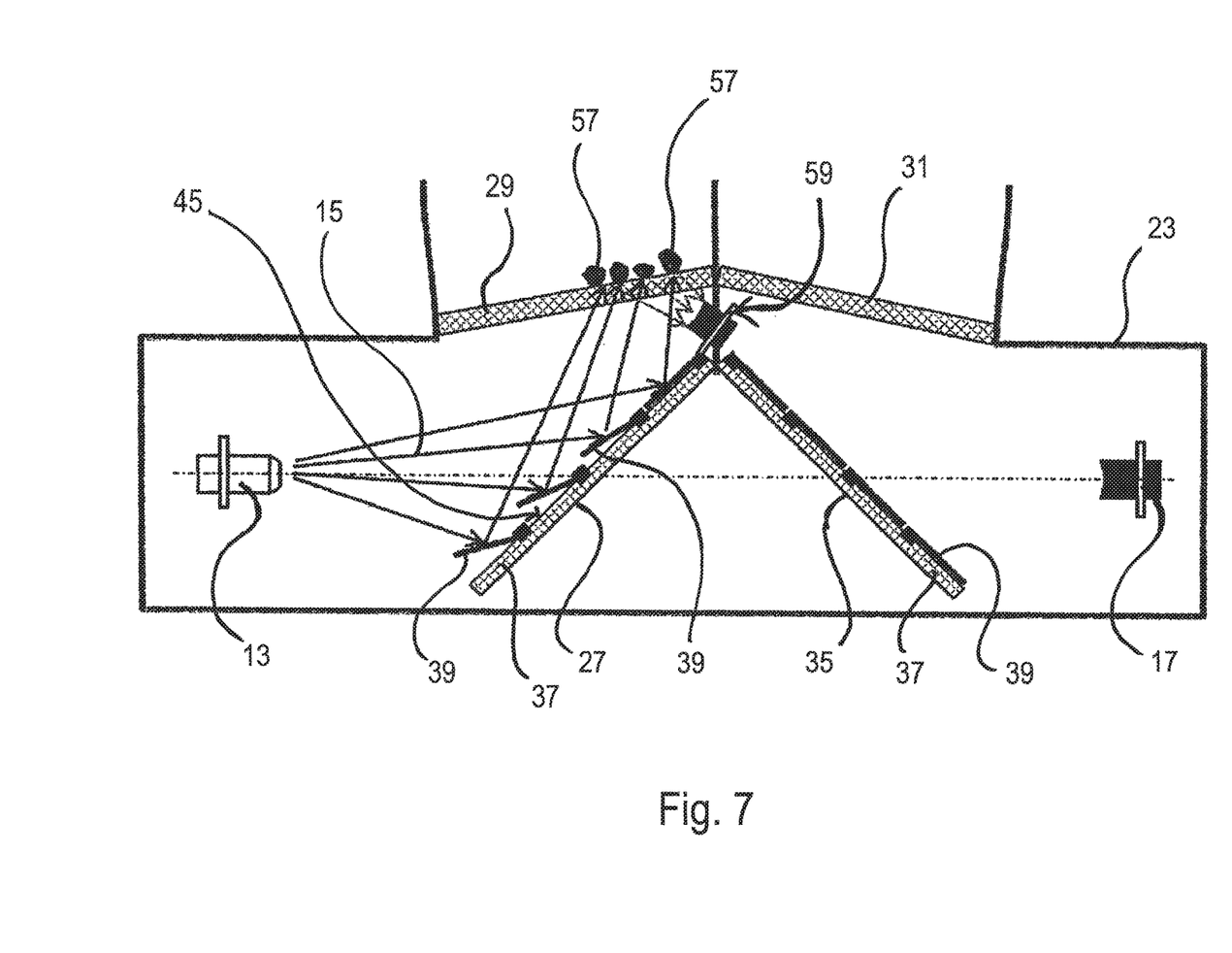
FIG. 7 shows a part of the sensor shown in FIG. 1 in a contamination test mode.

FIG. 7 shows a further operating state of an optical sensor 11 in accordance with the invention that serves for the checking of the first measurement window 29 for contamination. The first mirror unit 27 is in this respect set into an imaging state in which the micromirror elements 39 are tilted by different tilt angles with respect to the light incidence surface 45 such that the first mirror unit 27 acts in total as a concave mirror that focuses the transmitted light beams 15 on the first measurement window 29. A relatively high intensity of illumination thereby results at the first measurement window 29. Particulates 57 located at the first measurement window 29 scatter the light back, which is recognized by a contamination detector 59 in the form of a further light receiver. On an excessively strong contamination of the first measurement window 29, the control device outputs a suitable warning signal or maintenance signal.

Figure 8:
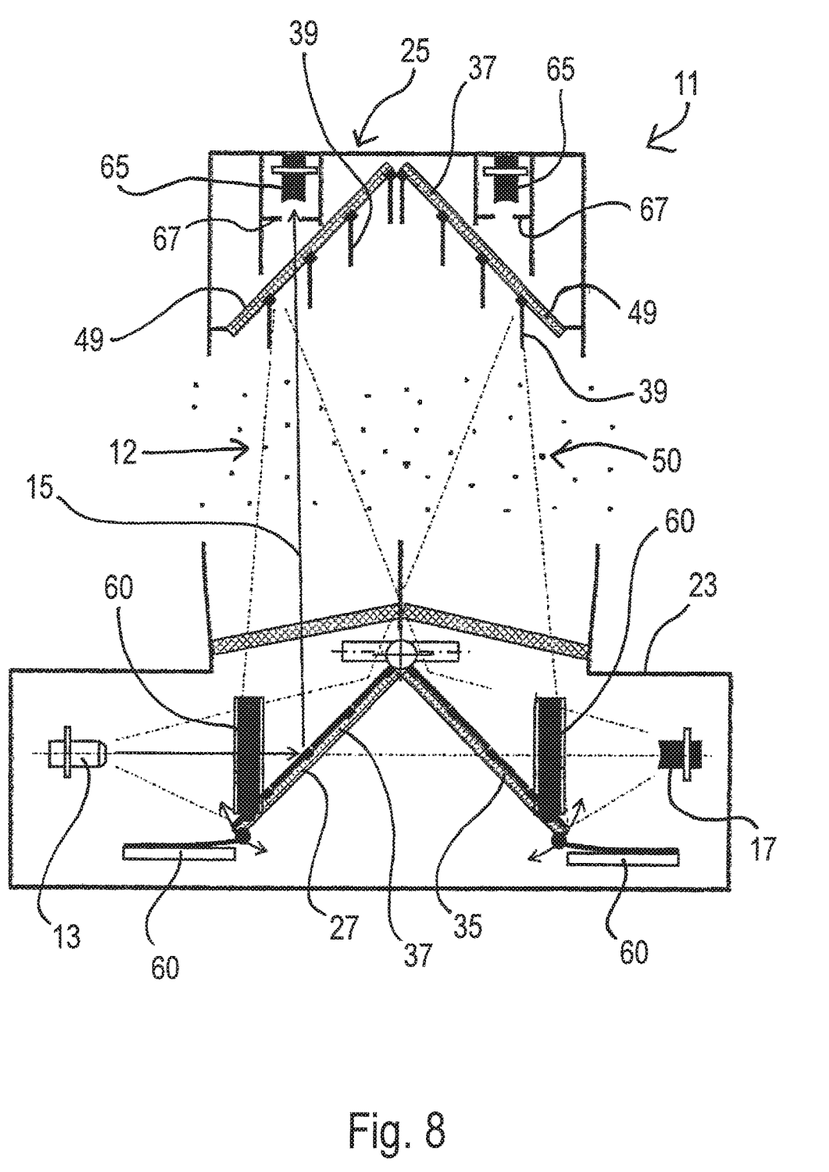
FIG. 8 shows an alternative embodiment of an optical sensor in accordance with the invention in an adjustment mode.

The optical sensor 11 in accordance with the invention shown in FIG. 8 is in principle designed as described above with reference to FIGS. 1-7. The first mirror unit 27 and the second mirror unit 35 are, however, pivotable about two pivot axes extending at right angles to one another by means of respective piezoelectric actuators 60. An exact alignment of the transmitted light beams 15 relative to the reflector 25 can take place in this manner. To facilitate the alignment procedure, position sensors 65 in the form of further light receivers are arranged in the reflector 25. Diaphragms 67 are associated with the position sensors 65 in the example shown. For the alignment, the reflector mirror units 49 are set, as shown, into the transmission state so that the position sensors 65 located behind the reflector mirror units 49 detect the transmitted light beams 15. When the intensity signal output by the respective position sensor 65 has a maximum value, the transmitted light beams 15 are ideally oriented.

The optical sensor 11 in accordance with the invention can be used in a variety of manners differing from the normal mode by a temporary operating of the first mirror unit 27, of the second mirror unit 35 and/or of the reflector mirror units 49 in transmission instead of in reflection. It is of particular advantage in this respect that mirror units on the basis of micromirror arrays have short switching times such that a fast cyclic change between different operating states is also possible, for example at frequencies from 1 Hz to 60 Hz. A quasi-continuous check of the unattenuated output intensity is thus also possible during the measurement, with unwanted data gaps being avoided.

REFERENCE NUMERAL LIST 11 optical sensor
12 measured zone
13 light transmitter
15 transmitted light beam
17 light receiver
19 received light beam
20 optical axis
23 base housing
25 reflector
27 first mirror unit
29 first measurement window
31 second measurement window
35 second mirror unit
37 substrate
39 micromirror element
45 light incidence surface
47 turbidity filter
49 reflector mirror unit
50 dust particle
55 scattered light beam
57 particulate
59 contamination detector
60 piezoelectric actuator
65 position sensor
67 diaphragm
α tilt angle

The invention claimed is:

1. An optical sensor comprising:
   a light transmitter for transmitting transmitted light beams into a measured zone;
   a light receiver for receiving received light beams from the measured zone;
   an evaluation unit for determining a property of the measured zone using the received light beams received by the light receiver;
   at least one mirror unit for scattering the transmitted light beams and/or the received light beams, with the at least one mirror unit comprising a plurality of micromirror elements having an at least regionally reflective surface and comprising an electrode arrangement electrically connected to the micromirror elements; and a control device that is configured to adjust the at least one mirror unit between at least two different functional states by controlling the electrode arrangement, wherein the at least one mirror unit further comprises an at least substantially transparent substrate at which the micromirror elements are arranged; and wherein the control device is configured to temporarily set the at least one mirror unit into a transmission state in which the micromirror elements are in an open position and light radiation incident onto the at least one mirror unit moves past the micromirror elements through the transparent substrate.

2. The optical sensor in accordance with claim 1, wherein the transmitted light beams move through the substrate of the at least one mirror unit without passing through the measured zone to the light receiver when the at least one mirror unit is set into the transmission state.

3. The optical sensor in accordance with claim 1, wherein the control device is configured to set the at least one mirror unit into the transmission state on the presence of a control criterion, a comparison criterion or a correction criterion.

4. The optical sensor in accordance with claim 1, wherein the micromirror elements are each tilted by a tilt angle with respect to a light incidence surface of the substrate when the at least one mirror unit is set into the transmission state.

5. The optical sensor in accordance with claim 4, wherein the tilt angle amounts to between 40° and 50°.

6. The optical sensor in accordance with claim 1, wherein the at least one mirror unit is arranged such that the micromirror elements are aligned at least substantially in parallel with a main direction of incidence of the transmitted light beams or of the received light beams when the at least one mirror unit is set into the transmission state.

7. The optical sensor in accordance with claim 1, wherein the control device is configured to temporarily set the at least one mirror unit into a reflection state in which the micromirror elements at least party cover a light incidence surface or a light exit surface of the at least one mirror unit.

8. The optical sensor in accordance with claim 7, wherein the control device is configured to temporarily set the at least one mirror unit into a reflection state in which the micromirror elements cover at least 75% of the light incidence surface or of the light exit surface.

9. The optical sensor in accordance with claim 7, wherein the control device is configured to temporarily set the at least one mirror unit into a reflection state in which the micromirror elements cover at least 90% of the light incidence surface or of the light exit surface.

10. The optical sensor in accordance with claim 7, wherein the control device is configured to adjust the at least one mirror unit cyclically between the reflection state and the transmission state during sensor operation.

11. The optical sensor in accordance with claim 7, wherein the light transmitter and the light receiver are arranged on a straight-line optical path and the measured zone is spaced apart from the straight-line optical path, with the at least one mirror unit decoupling the transmitted light beams from the straight-line optical path and deflecting them into the measured zone when it is set into the reflection state.

12. The optical sensor in accordance with claim 11, wherein the sensor comprises a further mirror unit that comprises an at least substantially transparent substrate having micromirror elements arranged thereat and that can be adjusted between a transmission state and a reflection state, with the further mirror unit coupling the received light beams exiting the measured zone into the straight-line optical path when it is set into the reflection state.

13. The optical sensor in accordance with claim 1, wherein the micromirror elements are individually controllable by respective individual electrodes of the electrode arrangement.

14. The optical sensor in accordance with claim 13, wherein the control device is configured to temporarily set the at least one mirror unit into a partly transmitting state in which only some of the micromirror elements are in an open position by controlling the individual electrodes.

15. The optical sensor in accordance with claim 13, wherein the control device is configured to temporarily set the at least one mirror unit into an imaging state by controlling the individual electrodes, in which state the micromirror elements are tilted by different tilt angles with respect to a light incidence surface or a light outlet surface of the substrate such that the at least one mirror unit overall defines a concavely or convexly arched mirror surface.

16. The optical sensor in accordance with claim 15, wherein the light transmitter and the at least one mirror unit are arranged in a closed housing that comprises at least one measurement window; and wherein the at least one mirror unit effects a focusing of the transmitted light beams on a surface of the measurement window when it is set into the imaging state.

17. The optical sensor in accordance with claim 1, wherein the light transmitter and the light receiver are arranged in a closed housing that comprises at least one measurement window, with the measured zone being located outside the housing and the sensor comprising a reflector that directs the light beams back into the housing after passing through the measured zone.

18. The optical sensor in accordance with claim 17, wherein the at least one mirror unit is integrated into the reflector.

19. The optical sensor in accordance with claim 1, wherein the optical sensor comprises at least one actuator for moving and/or rotating the at least one mirror unit.

20. An optical sensor comprising:

a light transmitter for transmitting transmitted light beams into a measured zone;

a light receiver for receiving received light beams from the measured zone;

an evaluation unit for determining a property of the measured zone using the received light beams received by the light receiver; at least one mirror unit for scattering the transmitted light beams and/or the received light beams, with the at least one mirror unit comprising a plurality of micromirror elements having an at least regionally reflective surface and comprising an electrode arrangement electrically connected to the micromirror elements; and a control device that is configured to adjust the at least one mirror unit between at least two different functional states by controlling the electrode arrangement, wherein the electrode arrangement comprises a plurality of individual electrodes by means of which the micromirror elements are individually controllable; and wherein the control device is configured to temporarily set the at least one mirror unit into an imaging state by controlling the individual electrodes, in which state the micromirror elements are tilted by different tilt angles with respect to a light incidence surface or a light exit surface of the at least one mirror unit such that the at least one mirror unit overall defines a concavely or convexly arched mirror surface.

* * * * *